(12) United States Patent
Palmon et al.

(10) Patent No.: US 9,297,804 B2
(45) Date of Patent: Mar. 29, 2016

(54) ASSAY AND KIT AND DEVICE FOR REMOVING AMYLASE FROM BODY FLUIDS

(75) Inventors: Aaron Palmon, Beit Nekofa (IL); Omer Doitch, Beer Sheva (IL); Doron Aframian, Jerusalem (IL)

(73) Assignees: YISSUM RESEARCH DEVELOPMENT COMPANY OF THE HEBREW UNIVERSITY OF JERUSALEM LTD., Jerusalem (IL); HADASIT MEDICAL RESEARCH SERVICES AND DEVELOPMENT LTD., Jerusalem (IL)

(*) Notice: Subject to any disclaimer, the term of this patent is extended or adjusted under 35 U.S.C. 154(b) by 210 days.

(21) Appl. No.: 12/451,196

(22) PCT Filed: May 1, 2008

(86) PCT No.: PCT/IL2008/000587
§ 371 (c)(1),
(2), (4) Date: Jan. 13, 2010

(87) PCT Pub. No.: WO2008/132747
PCT Pub. Date: Nov. 6, 2008

(65) Prior Publication Data
US 2010/0108611 A1    May 6, 2010

Related U.S. Application Data

(60) Provisional application No. 60/915,204, filed on May 1, 2007, provisional application No. 61/016,787, filed on Dec. 26, 2007.

(51) Int. Cl.
*B01D 15/08* (2006.01)
*G01N 33/573* (2006.01)

(52) U.S. Cl.
CPC ........ *G01N 33/573* (2013.01); *G01N 2333/926* (2013.01)

(58) Field of Classification Search
CPC . G01N 33/573; G01N 2333/926; G01N 1/34; G01N 1/4005; G01N 1/405; G01N 1/40; Y10T 436/25125; Y10T 436/255
USPC ........................ 436/63, 86, 94, 178, 177, 174
See application file for complete search history.

(56) References Cited

U.S. PATENT DOCUMENTS

| | | | |
|---|---|---|---|
| 4,923,565 A * | 5/1990 | Fuentes et al. | 162/72 |
| 5,186,839 A * | 2/1993 | Kimura et al. | 210/656 |
| 2006/0084182 A1* | 4/2006 | Farquharson et al. | 436/171 |

FOREIGN PATENT DOCUMENTS

| | | |
|---|---|---|
| EP | 0 486 325 | 5/1992 |
| GB | 1 453 484 | 10/1976 |
| GB | 2 085 159 | 4/1982 |

OTHER PUBLICATIONS

Martin, N. C. et al. "The sensitivity and specificity of Red-Starch paper for the detection of saliva." Science and Justice (2006) 46 97-105.*
Witt, Wolfgang et al. "Purification and properties of a starch granule-degrading [alpha]-amylase from potato tubers." Journal of Experimental Botany (1996) 47 1789-1795.*
Vitorino, Rui et al. "Identification of human whole saliva protein components using proteomics." Proteomics (2004) 4 1109-1115.*
Walker, Gwen J. et al. "The action of some alpha-amylases on starch granules." Biochem. J. (1963) 86 452-462.*
Wang, Young Y. et al. "A simple affinity spin tube filter method for removing high-abundant common proteins or enriching low-abundant biomarkers for serum proteomic analysis." Proteomics (2003) 3 243-248.*
Kawata, Kuniaki et al. "Gas chromatographic-mass spectrometric determination of hydropiliic compounds in environmental water by solid-phase extraction with activated carbon fiber felt." J. Chromatography A (2001) 911 75-83.*
Mendu, Damodara Rao et al. "Affinity chromatography of alpha-amylase from Bacillus licheniformis." Enzyme and Microbial Technology (2005) 37 712-717.*
International Search Report for PCT/IL2008/000587, mailed Aug. 27, 2008.
Written Opinion of the International Searching Authority for PCT/IL2008/000587, mailed Aug. 27, 2008.
Horst D Schell et al., "Alpha-Amylase Purification and Separation from Gluco-Amylase by Affinity Chromatography on Cross-Linked Amylose(CL-Amylose)", Analytical Letters, New York, NY, US, vol. 14, Jan. 1, 1981, pp. 1501-1514, XP009104249.
Barabino, et al., "Coupled Reactions of Immobilized Enzymes and Immobilized Substrates: Clinical Application as Exemplified by Amylase Assay," Clin. Chem., vol. 24, No. 8, 1978, pp. 1393-1398.
Horst D Schill et al., "Alpha-Amylase Purification and Separation from Gluco-Amylase by Affinity Chromatography on Cross-Linked Amylose(CL-Amylose)", Analytical Letters, New York, NY, US, vol. 14, Jan. 1, 1981, pp. 1501-1514, XP009104249.
Deutsch et al.; "An approach to remove alpha amylase for proteomic analysis of low abundance biomarkers in human saliva," Electrophoresis 2008, 29, 1-8.
Hu et al., "Human body fluid proteome analysis," *Proteomics*, 2006, vol. 6, pp. 6326-6353.

* cited by examiner

*Primary Examiner* — Christopher A Hixson
(74) *Attorney, Agent, or Firm* — Nixon & Vanderhye P.C.

(57) ABSTRACT

The invention is directed to separation of amylase from body fluid by contacting said body fluid with starch under conditions enabling binding between the amylase and the starch, separating between the starch-amylase bound complexes and the free components, thereby removing the bound amylase, and collecting the non-bound components.

6 Claims, 3 Drawing Sheets

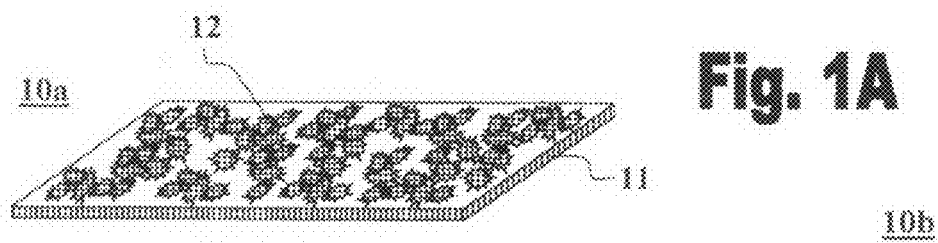
Fig. 1A
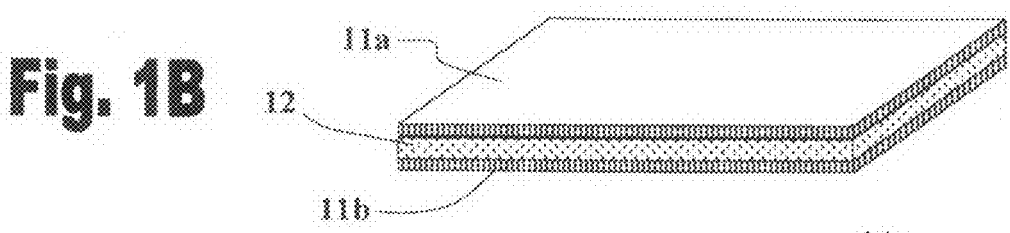
Fig. 1B
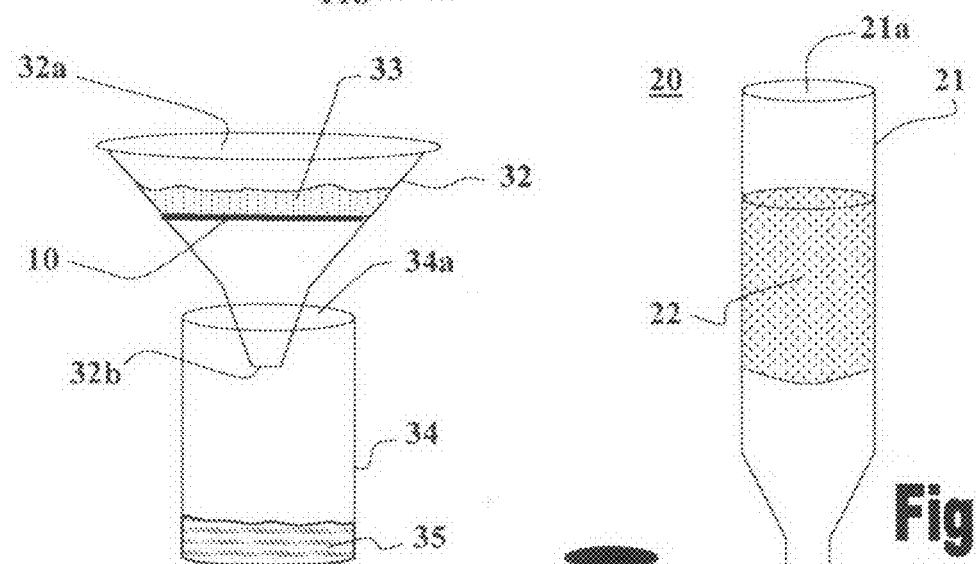
Fig. 2
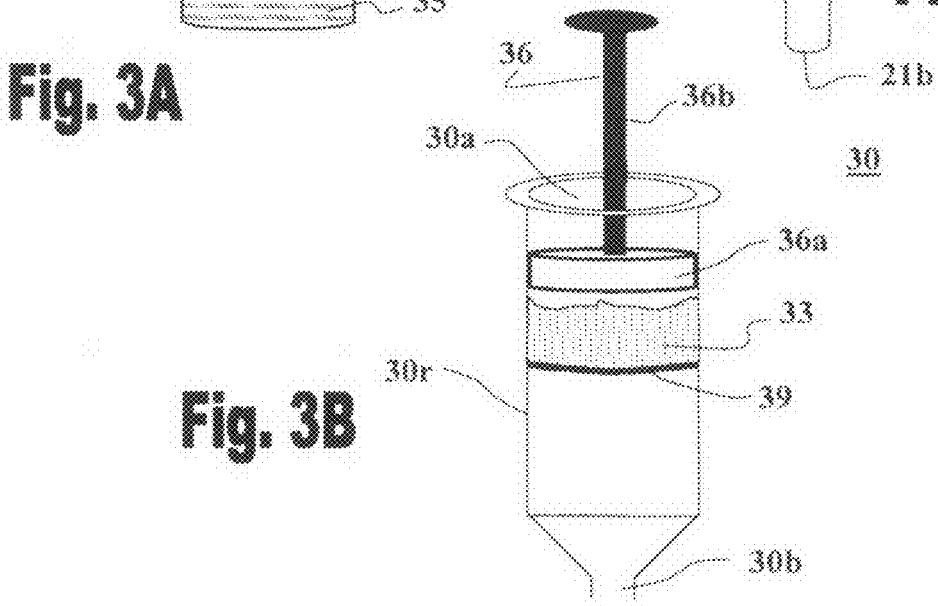
Fig. 3A
Fig. 3B

ASSAY AND KIT AND DEVICE FOR REMOVING AMYLASE FROM BODY FLUIDS

This application is the U.S. national phase of International Application No. PCT/IL2008/000587 filed 1 May 2008, which designated the U.S. and claims priority to U.S. Application Nos. 60/915,204, filed 1 May 2007 and 61/016,787, filed 26 Dec. 2007, the entire contents of each of which are hereby incorporated by reference.

FIELD OF THE INVENTION

The present invention relates to removal and/or collection of amylase from body fluids, in particular from oral fluids.

BACKGROUND OF THE INVENTION

Lately there is an increased interest in finding disease biomarkers in human body fluids such as blood plasma, urine, CSF and also oral fluids. Oral fluids can be easily and non-invasively collected with low collection, storage and shipment costs, and thus allow vast epidemiologic screening. One main drawback in oral fluid protein identification is the very high relative amount of α-Amylase protein (comprising up to 60% of saliva proteins, the major component of oral fluids) which masks the presence of other protein components.

The α-amylases (EC 3.2.1.1, CAS#9014-71-5, alternate names: 1,4-α-D-glucan glucanohydrolase; glycogenase) are calcium metalloenzymes, completely unable to function in the absence of calcium. By acting at random locations along the starch chain, α-amylase breaks down long-chain carbohydrates, ultimately yielding maltotriose and maltoe from amylose, or maltose, glucose and "limit dextrin" from amylopectin. Because it can act anywhere on the substrate, α-amylase tends to be faster acting than β-amylase. In animals, it is a major digestive enzyme.

U.S. Pat. No. 5,576,181 to Torrens et al., is aimed at reducing the amount of amylase by using monoclonal antibodies against salivary amylase for the purpose of detecting remaining pancreatic amylase activity. However, this method is of low practical utility since antibodies are expensive and difficult to store in a stable manner for long periods of time; consequently, this method has not gained wide acceptance.

Therefore there is a need for cost effective means for removing amylase from body fluids, in particular, oral fluids.

It is an object of the present invention to provide an assay, kit, device and method, for efficiently removing amylase from body fluids.

It is another object of the present invention to provide methods and devices for minimizing, or preventing, screening effects caused by α-amylases protein in the laboratory assay of oral fluids.

It is a further object of the present invention to provide an assay, kit, device and method, for collecting amylase from oral fluids.

Other objects and advantages of the invention will become apparent as the description proceeds.

SUMMARY OF THE INVENTION

The inventors hereof developed a device that removes amylase from oral fluids, as well as from other body fluids, such as sweat, lacrimal fluid, gastro-intestinal fluid, pancreatic fluids, serum and urine, by means of a filtering device loaded with starch, which is the amylase substrate. By means of this technology, the fluid containing the amylase is passed through the filter containing amylase substrate, a vast amount of the amylase is bound to its substrate and the resulting filtrate has a correspondingly decreased amount of enzyme.

The advantages of the present invention, inter alia, are its low cost, higher durability, ease of use, higher sample volume, broader spectrum of amylase removal, and its ability to remove fluid debris (eliminating the need for pre-separation treatment such as centrifugation).

In one aspect, the present invention provides a method for removing amylase from a body fluid, said method comprising:
  contacting said body fluid with starch under conditions enabling binding between the amylase and the starch;
  separating between the starch-amylase bound complexes and the free components thereby, removing the bound amylase; and
  collecting the non-bound components.

The term "removing" may refer to complete removal, as well as to partial reduction in the amylase concentration/activity as compared with untreated body fluid.

The term "amylase", refers to alpha, beta and gamma amylase; preferably this term refers to α-amylase.

The term "body fluid" may refer to oral fluids such as saliva as well as sweat, lacrimal fluid, gastro-intestinal fluid, pancreatic fluid, serum and urine.

The term "starch" is used herein in general to include any substrate of the amylase whether isolated from a natural source or synthetically produced. Chemically, natural starch consists of two types of molecules, amylose (normally 20-30%) and amylopectin (normally 70-80%). Both consist of polymers of α-D-glucose units in the 4C1 conformation. In amylose these units are linked -(1 4)-, with the ring oxygen atoms all on the same side, whereas in amylopectin about one residue in every twenty or so is also linked -(1 6)- forming branch-points. The relative proportions of amylose to amylopectin and -(1 6)- branch-points both depend on the source of the starch, e.g. amylomaizes contain over 50% amylose whereas 'waxy' maize has almost none (~3%).

In one option in accordance with the present invention, also referred to herein as the "immobilized starch embodiment" the starch is immobilized on a substrate. This may be achieved by any manner such as loading the starch on a filter paper, onto resins in a column, binding chemically the starch onto another substrate etc. Then the body fluid is allowed to come into contact with the immobilized starch under suitable conditions, for example by filtering the fluid through the starch loaded paper, by passing it through the starch loaded column, or by contacting it with the starch bound substrate.

In accordance with this aspect the present invention concerns a method for removing amylase from a body fluid, the method comprising:
  contacting the body fluid with an immobilized starch under conditions enabling binding between the amylase and the starch, thereby immobilizing the amylase on the substrate; and
  collecting the non-bound components.

In another embodiment, also referred to herein as the "free starch embodiment", which is preferred according to the invention, the starch is "free" (i.e. present in the assay medium in a free state, unbound to any substrate) and the amylase-starch bound complex is separated from the remaining fluid by size separation such as through a filter with a predefined size cutoff.

In accordance with this aspect the present invention provides a method for removing amylase from a body fluid, the method comprising:

contacting the body fluid with starch present in a liquid medium under conditions enabling binding between the amylase and the starch;

separating between the starch-amylase complexes and the free components by filtration thereby removing the bound amylase; and collecting the non-bound components.

In both cases the contacting of the body liquid with the starch should be done under conditions enabling binding including pH (e.g., of about pH=7), temperature (e.g., about 15-35 c), and rate of passage (e.g., about 0.5-2 ml/min).

Then the fluid/filtrate which is not bound to the starch (both in the "immobilized starch embodiment" and in the "free starch embodiment") is collected thereby obtaining a fluid with reduced amylase concentrations, which can be used for subsequent purposes, such as for testing of additional agents, bio-markers, or hormones presence in the fluid.

The present invention also provides a device and cassette that may be used to implement the "immobilized starch embodiment".

In accordance with this aspect of the present invention for removing amylase from a body fluid, the device comprises a receptacle for holding the body fluid, being in fluid communication with a substrate having starch immobilized thereon.

In one embodiment, the fluid is passed from the receptacle through the substrate with the immobilized starch, and is collected in a collecting element, due to the force of gravity, or other natural forces such as capillary forces.

In another embodiment, the device has an integral flow-facilitation means, such as a syringe attached to the fluid holding receptacle, or a vacuum source attached to the collecting element.

By yet another option the device is capable of connecting to flow facilitation means, such as having a suitable connector to a positive pressure element (such as syringe), attached to the body fluid receptacle, or capable of being attached to a vacuum source in the fluid collecting element.

The fluid collecting element may be an integral part of the device, or may be a separate element.

The substrate may be as defined above: filter (such as filter paper) loaded with starch, resin of a column loaded with starch, solid substrate having thereon immobilized starch etc.

The present invention also concerns a substrate with immobilized starch adapted for insertion into the above device such as a cassette of filter paper loaded with starch, a column comprising loaded starch, solid substrate with immobilized starch etc.

In accordance with the "free substrate embodiment" the present invention also provides a device for removing amylase from a body fluid, the device comprising: a receptacle for holding the body fluid and also for holding the starch, the receptacle being in fluid communication with a filter for separation of amylase-starch bound complexes from the body fluid.

In accordance with one embodiment, the fluid is passed from the receptacle through the filter to a collecting element by means of gravity, or capillary, forces.

In another embodiment, the device has an integral flow-facilitation means, such as a syringe attached to the fluid holding receptacle, or a vacuum source attached to the collecting element.

In yet another embodiment, the device is capable of being connected to flow facilitation means, such as having a suitable connector to a positive pressure element (such as syringe) attached to the body fluid receptacle, or capable of being attached to a vacuum in the fluid collecting element.

The fluid collecting element may be an integral part of the device, or may be a separate element.

As the filter is intended to separate the amylase-starch complex from the remaining components, said filter should have a cut-off size of 0.45 to 50 micrometer.

Examples of suitable filters are Whatman FP 30/0.45 and Whatman GF/C.

In accordance with a preferred embodiment of the invention the amylase removing device is composed of a plastic syringe (e.g., 1 ml for 0.5 ml oral fluids, 10 ml for 4 ml oral fluids) ending in an 0.45-50 µm filter (e.g., made of Whatman FP 30/0.45 or Whatman GF/C). The syringe is filled with an appropriate amount of amylase substrate (e.g., potato starch, Sigma S2630, 600 mg for 1 ml syringe, 2.3 gr. for 10 ml syringe). Water is first passed through the device using manual pressure in order to moisture the substrate. Then, the oral fluid sample is hand pressure filtered through the syringe. The filtrate thereby obtained is Substantially amylase free.

By another aspect the present invention concern a method for obtaining amylase from saliva or any body fluid.

The method is essentially as described above but in this case the material that is collected is the bound fraction containing the amylase.

In accordance with this aspect the present invention provides a method for obtaining amylase from a body fluid, the method comprising:

contacting the body fluid with a substrate under conditions enabling binding between the amylase and the starch;

separating between the starch-amylase bound complexes and the free component to obtain said complexes; and separating the amylase from the starch.

The method may be used with immobilized starch and in such a case the invention concerns a method for obtaining amylase from a body fluid, the method comprising:

contacting the body fluid with an immobilized starch under conditions enabling binding between the amylase and the starch, thereby immobilizing the amylase on the substrate;

removing unbound components; and separating the amylase from the substrate.

The method may be further used with "free starch" and in such a case the invention concerns a method for obtaining amylase from a body fluid, the method comprising:

contacting the body fluid with starch present in a fluid under conditions enabling binding between the amylase and the starch;

separating between the starch-amylase bound complexes and the free components by filtration thereby removing the non-bound components;

separating between the starch and the amylase.

The devices of the present invention disclosed hereinabove and described in more detail hereinbelow may also be used for obtaining the amylase, for example by obtaining the amylase-starch complex and separating the amylase from the starch.

Separation of the amylase from the starch can be achieved for example by soaking/passing the amylase-starch complex with/in acidulated water or by contact with SDS-Mercapto-ethanol solution.

According to yet another aspect the invention is directed to an amylase-binding filter adapted for insertion into a device of the present invention, comprising a porous media (e.g., having pore of about 45-50µ) having at least one layer of starch applied over one of its sides, wherein said at least one layer of starch is capable of being used as a binder for removing amylase from a fluid passed therethrough. Optionally, the amylase filter may further comprise an additional porous media, such that the at least one layer of starch is sandwiched between the porous medias of said filter.

According to a further aspect the invention is directed to an amylase filter device comprising a hollow element having first and second openings connected by a passage and amylase collecting means comprising starch, said amylase collecting means is disposed inside said passage such that it occupies a cross-section of said passage, such that fluids passed through said hollow element are forced to pass through said amylase collecting means. The amylase collecting means may be implemented by any one of the amylase filters of the invention. The amylase filter device may further comprise a pressure source capable of being sealably connected to the hollow element for forcing fluids introduced thereinside to pass through the amylase collecting means.

Optionally, the hollow element is a column and the amylase collecting means is a resin packed therein, said resin comprising immobilized starch.

Preferably, the hollow element is a syringe barrel, and wherein a syringe plunger is utilized for passing fluids introduced into said syringe barrel through the amylase collecting means.

BRIEF DESCRIPTION OF THE DRAWINGS

The present invention is illustrated by way of example in the accompanying drawings, in which similar references consistently indicate similar elements and in which:

FIGS. 1A and 1B schematically illustrate possible filter implementations loaded with starch;

FIG. 2 schematically illustrates an implementation of a resin column separation device;

FIGS. 3A and 3B schematically illustrate examples of filtration devices employing filter implementations of the invention;

DETAILED DESCRIPTION OF PREFERRED EMBODIMENTS

Figure 4:
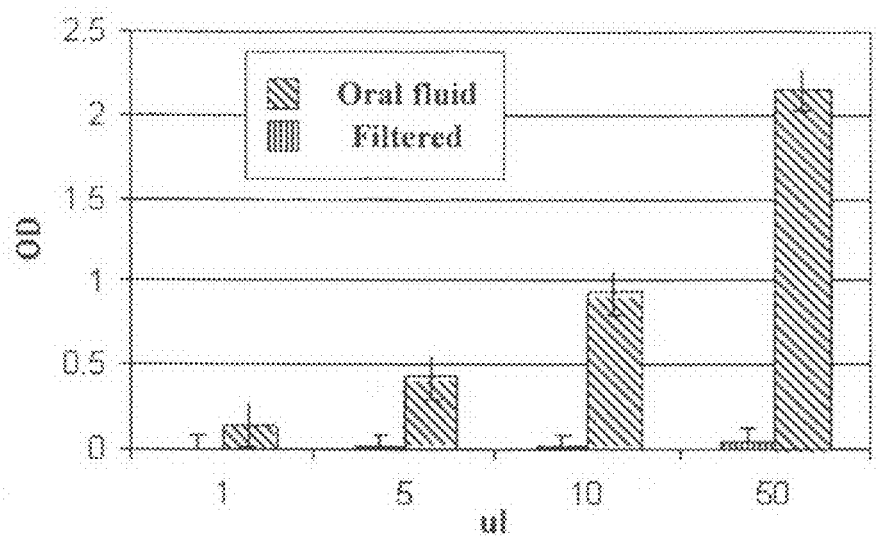
FIG. 4 shows amylase activity before and after separation obtained with a syringe based embodiment of the invention.

The present invention will be now described with reference to the accompanying figures. The amylase removal/extraction implementations illustrated in FIGS. 1 to 3 exemplify preferred embodiments which may be varied and modified according to specific requirements without departing from the spirit and scope of this invention.

FIGS. 1A and 1B schematically illustrate possible implementations wherein a porous media comprising starch is employed for filtering amylase from a body fluid. In the amylase filter 10a illustrated in FIG. 1A, the layer of starch 12 loaded on a porous media 11 is used as a binder for removing amylase from an amylase containing fluid passed therethrough. Porous media 11 may be manufactured from a type of filter paper, for example, such as, but not limited to, Whatman FP 30/0.45 or Whatman GF/C. The layer of starch 12 may be prepared from a type of partially hydrophilic starch, and it may be applied over at least one side of porous media 11, and it is preferably applied such that the surface area of at least one side of porous media 11 is more or less uniformly covered by it.

Another implementation of an amylase filter 10b is illustrated in FIG. 1B, wherein a layer of starch 12 is sandwiched between two porous media sheets, 11a and 11b. Porous media sheets 11a and 11b may be manufactured from similar materials as indicated above for amylase filter 10a shown in FIG. 1A.

Amylase filters 10a and 10b may be provided in form of separate filter sheets, or as a continuous rolled strip provided in a form of a cassette.

FIG. 2 schematically illustrates an implementation of a separation device 20 constructed in the form of a resin column. Separation device 20 is comprised of a vertical column comprising column inlet 21a and an outlet 21b having a passage in between, a cross-sectional portion of which is partially filled with a starch binder 22. In use, an amylase comprising fluid (not shown) is introduced into device 20 via its inlet 21a, and it is forced to pass through the starch binder 22 towards outlet 21b, by force of gravitation, or by pressure/vacuum applying means (not shown). The fluid obtained at the outlet 21b, from which significant amylase portions were removed by the starch binder 22, may be collected into a receptacle (not shown).

Column 21 is preferably made from a type of plastic material, but other suitable materials may be equally used. The diameter of column 21 may generally be in the range of 3 to 10 mm, preferably about 5 mm, and its length is preferably about 4-10 cm. The thickness of the starch binder 22 inside column 21 may be about 0.5 to 3 cm, and it is preferably placed towards outlet 21b of column 21. The lower section of column 20 may taper downwardly in order to funnel the fluids passing therethrough to outlet 21b.

FIGS. 3A and 3B schematically illustrate filtration devices in which amylase filters 10, such as 10a or 10b respectively shown in FIGS. 1A and 1B, of the invention are employed. The device shown in FIG. 3A comprises a funnel 32 a cross-sectional part of which is occupied by an amylase filter 10, such that amylase containing fluid 33 introduced thereinto via funnel inlet 32a is forced to pass through amylase filter 10 towards the funnel outlet 32b. The fluids obtained at funnel outlet 32b are collected by receptacle 34, as indicated by numeral 35. Funnel 32 may be manufactured from any suitable material, as used in the funnel manufacturing industry, and its geometrical dimensions may be similar to those of standard laboratory funnels.

FIG. 3B shows an amylase filtration implementation 30 constructed in the form of a syringe comprising a syringe barrel 30r having an amylase filter 39 occupying a cross-sectional section thereof. Amylase filter may be implemented by amylase filter 10a or 10b described hereinabove, or alternatively, it may be implemented by a porous medium disposed inside barrel 30r and having a layer of starch disposed thereon. In use, a fluid comprising amylase 33 is introduced into syringe barrel 30r via opening 30a, and the syringe plunger 36a is thereafter also inserted thereinto and advanced thereinside by means of plunger shaft 36b, such that the amylase comprising fluid 33 is forced to pass through amylase filter 39. The fluid passed through amylase filter 39 is obtained through the funneled outlet 30b of syringe barrel 30r. It is noted that other pressure applying means may be used to force amylase comprising fluid to pass through amylase filter 39B, such as, for example, a pressure source (not shown) connected to opening 30a. Alternatively, vacuum may be applied via funneled outlet 30b of syringe barrel 30r (e.g., by fluid collecting receptacle sealably attached thereto).

Syringe implementation 30 shown in FIG. 3B may be manufactured from standard materials, and in standard sizes, as used in the syringe manufacture industry. However, the length of plunger shaft 36b is preferably adjusted in order to prevent excess advancement of plunger 36a pass the portion of the barrel comprising the amylase filter 39. The diameter of syringe 30 may generally be in the range of 3 to 10 mm, preferably about 5 mm. Amylase filter may be implemented by a layer of porous material (e.g., having pores of about 45-50μ) circumferentially attached thereinside and having a layer (e.g., about 0.5-3 cm) of starch, preferably a type of partially hydrophilic starch, disposed thereon.

Example 1

Figure 5A:
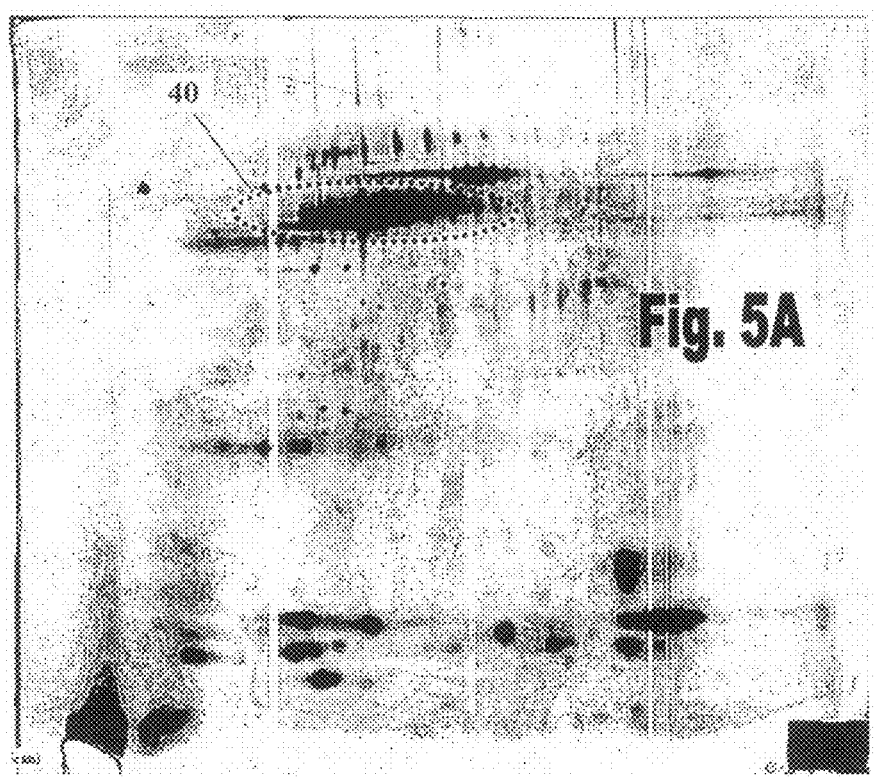
FIGS. 5A and 5B respectively show proteomic analysis results of oral fluids protein extract before and after amylase removal (amylase area encycled)
Figure 5B:
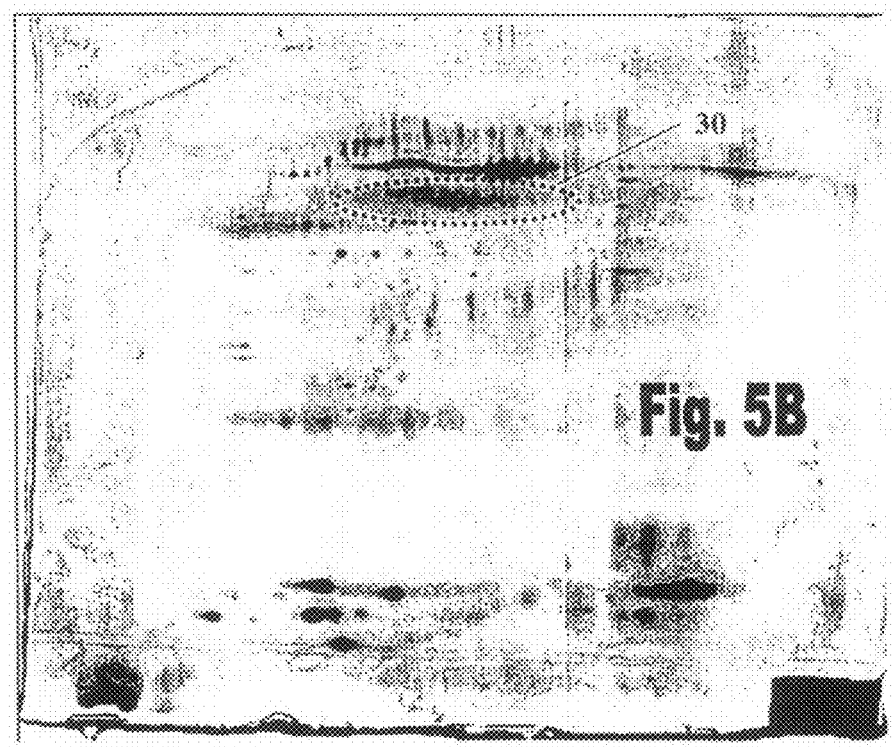

Oral fluids were collected and filtered through a preferred device of the invention being a syringe filed with starch and ended with filter paper. Then the filtrated fluid was measured for amylase activity and subjected to proteomic analysis for protein spot identification. The results shown in FIG. 4 show that amylase activity was reduced almost to below the level of detection. FIGS. 5A and 5B show proteomic analysis in which selective removal of protein spots corresponding to amylase protein is demonstrated. These results demonstrate that amylase protein can be removed from oral fluids.

Example 2

Obtaining Amylase from Saliva

Figure 6:
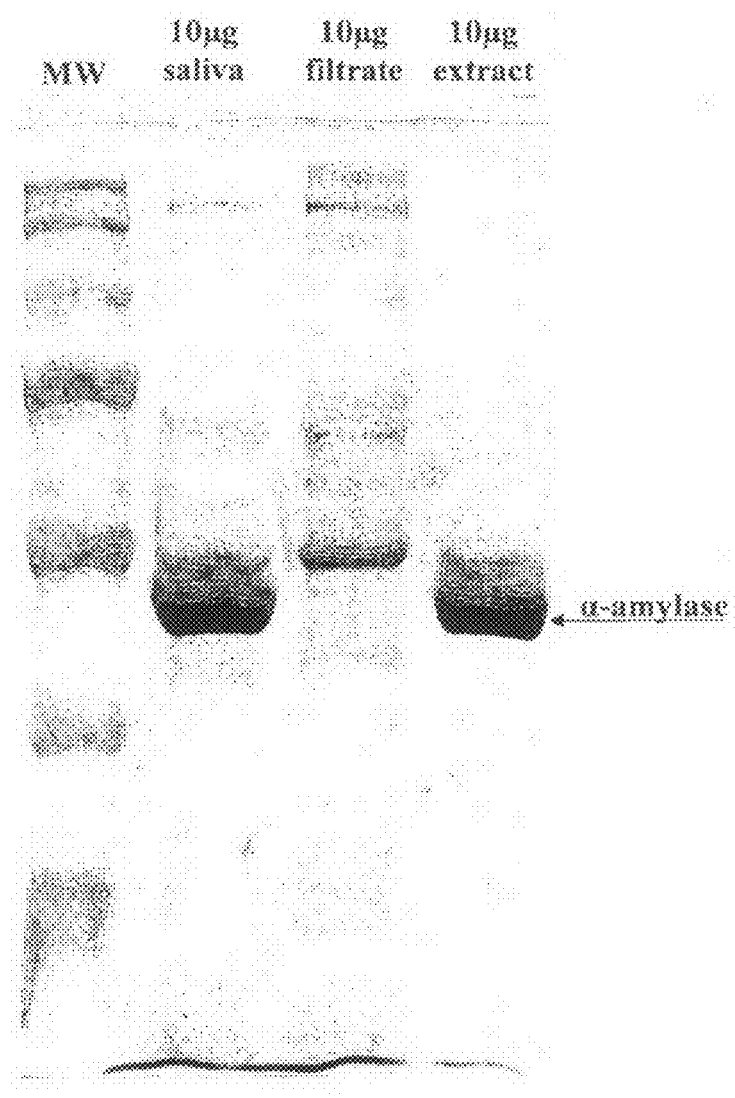
FIG. 6 shows SDS-PAGE separation of whole saliva, saliva depleted of amylase and captured amylase.

The amylase removing device described above was also used to capture and obtain amylase from saliva (or any other body fluid). After filtrating the saliva as described above (resulting in the formation of amylase-starch complexes) amylase is extracted from the potato starch matrix by means of soaking the matrix in water for 30 min (25% recover and active), or by the addition of SDS-Mercaptoethanol solution or by passing acidulated water for 2 minutes (>90% recovery). Alpha amylase identity was verified by MS, as shown in FIG. 6.

It should be noted that the embodiments exemplified in the Figures are not intended to be to scale and are in diagram form to facilitate ease of understanding and description. All of the abovementioned parameters are given by way of example only, and may be changed in accordance with the differing requirements of the various embodiments of the present invention. Thus, the abovementioned parameters should not be construed as limiting the scope of the present invention in any way.

The above examples and description have of course been provided only for the purpose of illustration; and are not intended to limit the invention in any way. As will be appreciated by the skilled person, the invention can be carried out in a great variety of ways, employing more than one technique from those described above, all without exceeding the scope of the invention.

The invention claimed is:

1. A method for removing α-amylase from an oral fluid sample in order to minimize or prevent the screening effects caused by said α-amylase in a laboratory assay of said oral fluid sample, said method comprising:
    contacting said oral fluid sample with starch under conditions enabling binding between the α-amylase and said starch, at a temperature of 15-35° C., wherein said starch is not bound to resin and is not chemically bound to another substrate;
    separating the starch-amylase bound complexes from the free components, thereby removing the bound α-amylase;
    wherein said contacting and said separating are achieved by means of passing said oral fluid through a filtering device loaded with said starch, wherein said starch is immobilized, applied or disposed on or above a filter that is a sheet of porous media;
    collecting the non-bound components in a filtrate having a decreased amount of α-amylase, thereby obtaining a fluid with a reduced α-amylase concentration; and
    using said fluid with reduced α-amylase concentration for testing of agents, bio-markers or hormones present in the fluid.

2. The method according to claim 1, wherein the filter is a filter paper.

3. A method according to claim 1, wherein the filtering device through which the sample is passed is a syringe comprising a syringe barrel having an amylase filter occupying a cross-sectional section thereof, wherein the sample is introduced into the syringe barrel and thereafter a syringe plunger is also inserted thereinto and advanced thereinside by means of plunger shaft, such that the sample is forced to pass through said amylase filter.

4. A method according to claim 1, wherein the layer of starch is sandwiched between two porous sheets.

5. A method according to claim 3, wherein the starch is potato starch.

6. A method according to claim 1, wherein said passing of said oral fluid is at a rate of 0.5-2 ml/min.

* * * * *